United States Patent [19]

Nicolet

[11] 4,321,214
[45] Mar. 23, 1982

[54] EXTREME PURIFICATION OF SULFONIC-TYPE ACIDS FOR PROCESSING TO HIGHLY OVERBASED METAL SULFONATES

[75] Inventor: Charles F. Nicolet, Naperville, Ill.

[73] Assignee: Standard Oil Company (Indiana), Chicago, Ill.

[21] Appl. No.: 760,014

[22] Filed: Jan. 17, 1977

Related U.S. Application Data

[63] Continuation-in-part of Ser. No. 662,975, Mar. 1, 1976, abandoned, which is a continuation-in-part of Ser. No. 562,887, Mar. 28, 1975, abandoned.

[51] Int. Cl.³ .................... C07B 13/00; C07C 143/24
[52] U.S. Cl. .......................... 260/504 R; 260/505 P; 260/504S
[58] Field of Search ............ 260/505 S, 505 P, 505 N, 260/504 R

[56] References Cited

U.S. PATENT DOCUMENTS

| | | | |
|---|---|---|---|
| 3,007,868 | 11/1961 | Eck | 260/504 |
| 3,050,464 | 8/1962 | Brown | 260/504 |
| 3,496,224 | 2/1970 | Ayers | 260/505 P |
| 3,720,707 | 3/1973 | Vanderlinden | 260/505 P |
| 3,798,261 | 3/1974 | Kemp | 260/504 |

*Primary Examiner*—Alan Siegel
*Attorney, Agent, or Firm*—Mark J. DiPietro; William T. McClain; William H. Magidson

[57] ABSTRACT

A purification process of crude oil soluble hydrocarbon sulfonic acid mixtures which comprises washing the crude oil soluble hydrocarbon sulfonic acid with water, contacting the washed, partially pure oil soluble hydrocarbon sulfonic acid with an excess of calcium carbonate to neutralize entrained sulfuric acid and adsorb impurities, removing the resulting calcium sulfate along with the remaining calcium carbonate, and recovering the pure sulfonic acid. Sulfonic acid produced in this manner is substantially free of impurities. The sulfonic acid is ideal for overbasing to high Total Base Number (TBN) sulfonate.

8 Claims, No Drawings

EXTREME PURIFICATION OF SULFONIC-TYPE ACIDS FOR PROCESSING TO HIGHLY OVERBASED METAL SULFONATES

CROSS-REFERENCE TO RELATED APPLICATIONS

This application is a continuation-in-part of application Ser. No. 662,975, filed Mar. 1, 1976 now abandoned, which is a continuation-in-part of Ser. No. 562,887, filed Mar. 28, 1975 now abandoned.

BACKGROUND OF INVENTION

This invention relates to a process to purify chemical intermediates. The chemical intermediate is oil soluble hydrocarbon sulfonic acid. The oil soluble hydrocarbon sulfonic acid can be processed with alkali earth metal bases into overbased sulfonate. The overbased sulfonate has many uses. Commonly, overbased sulfonates can be used as lubricant additives and fuel additives.

Lubricating oils tend to deteriorate under conditions of use in present day diesel and automotive engines. Deterioration is caused by acidic materials produced in engine operation, and by sludge and resinous materials which form during engine operation. Certain oil additives are used to neutralize the acidic material and to suspend damaging sludge and resin.

Highly overbased metal sulfonates have acid neutralization properties and detergent properties which suspend sludge. Overbased sulfonates contain more alkaline earth metal base than is necessary to neutralize the sulfonic acid.

Highly overbased sulfonates have been used in many lubricating oil compositions. To produce highly overbased sulfonates, pure sulfonic acid is necessary. Purification processes in the art produce sulfonic acids which contain impurities at harmful levels. The impurities can be sulfuric acid, water, reaction sludge, and calcium sulfate among others.

The impurities found in the sulfonic acid prevent successful overbasing, cause deterioration of the sulfonic acid during processing, force the use of only certain grades of metal bases for overbasing, and reduce the time the sulfonic acid and the sulfonates can be stored.

Severe engine environments caused by air pollution modifications require better oil additives. Improvements in the quality of sulfonic acid result in improved oil additives.

SUMMARY OF THE INVENTION

This invention pertains to a process for producing extremely pure oil soluble hydrocarbon sulfonic acid. The sulfonic acid produced having properties and purity superior to sulfonic acid produced by prior art.

In accordance with this invention are process steps sufficient to produce extremely pure sulfonic acid. The steps comprise washing the crude oil soluble hydrocarbon sulfonic acid with water, contacting the partially pure oil soluble hydrocarbon sulfonic acid with calcium carbonate to neutralize sulfuric acid and adsorb impurities, separating the solid calcium sulfate along with remaining calcium carbonate and adsorbed impurities, and recovering the pure sulfonic acid free of sulfuric acid, calcium sulfate, water and other impurities.

DESCRIPTION OF THE PREFERRED EMBODIMENTS

The crude sulfonic acids which can be treated in accordance with the process of this invention include (1) alkylaromatic sulfonic acids such as polypropyl alkylates of benzene sulfonic acids, naphthalene sulfonic acids and anthracene sulfonic acids; (2) straight chain polypropenyl and polybutenyl sulfonic acids; and (3) mixtures of the polyalkyl aromatic sulfonic acids and poly-alkenyl sulfonic acids referred to above within the subsections (1) and (2).

Organic compounds within the broad class of alkylaromatics include such compounds as (1) polypropyl aromatics, (2) poly-1-butyl aromatics, (3) polyisobutyl aromatics, (4) poly-2-butyl aromatics, (5) polyethyl aromatics, (6) copolymer propyl and 1-butyl aromatics, (7) copolymer propyl and isobutyl aromatics, (8) copolymer propyl and 2-butyl aromatics, (9) copolymer propyl and ethyl aromatics, (10) copolymer ethyl and 1-butyl aromatics, (11) copolymer ethyl and isobutyl aromatics, (12) copolymer ethyl and 2-butyl aromatics, (13) copolymer 1-butyl and isobutyl aromatics, (14) copolymer 1-butyl aromatics and (15) copolymer isobutyl and 2-butyl aromatics. The number average molecular weight of these compounds ranges from about 400 to about 900.

The term "aromatics" are used hereinabove and throughout this application is intended to include mono- and polycyclic aromatic hydrocarbons such as benzenes, naphthalenes and anthracenes.

The preferred alkylaromatics include polypropyl, polybutyl, and copolymeric propyl-1-butyl derivatives of benzene; and straight chain polypropenyl derivatives. Especially preferred are polypropyl benzenes wherein the alkyl moiety has a number average molecular weight of about 580, or about 870, polydispersion of about 1.2 to about 1.7. The polydispersion of a polymer is a number calculated by dividing the weight average molecular weight of the polymer by the number average molecular weight. This number signifies the range of molecular weights present in the polymer.

Calcium carbonate used in this process is crushed limestone. Calcium carbonate when crushed exhibits greater acid neutralizing power and adsorbtive power. A particle size which is preferred ranges from about 0.2 to about 5 microns.

The preferred type of hydrocarbon lubricating oils contemplated in the practice of this invention are solvent extracted lubricating oils such as SX-5W, which do not contain additives.

The term inert organic solvent includes hexane and heptane and like compounds with boiling points less than 175° F. Hexane is the preferred solvent for this process. The solvent is inert to the sulfonating agent, calcium carbonate, calcium sulfate and sulfonic acid.

The term crude oil soluble hydrocarbon sulfonic acid reaction mixture includes mixtures present in sulfonation reactors after the sulfonation reaction is complete. These mixtures generally are made up of unreacted sulfonation agent, unsulfonated hydrocarbon, the sulfonated hydrocarbon, impurity caused by reaction conditions and an inert organic solvent carrier, if necessary. Examples of sulfonation agents are sulfur trioxide, oleum, and fuming sulfuric acid.

Any alkyl aromatic sulfonic acid, straight chain alkenyl sulfonic acid and mixtures thereof, of the type referred to in this application, can be treated in accordance with the novel and successful process of this invention.

The process in this disclosure comprises washing the crude sulfonic acid mixture with water, and contacting the sulfonic acid with calcium carbonate to selectively neutralize and remove sulfuric acid impurities remaining in the organic sulfonic acid phase. The preferred embodiment, described in detail, begins with adding a volume of water to a crude mixture of sulfonic acid in hexane to reduce the sulfuric acid strength to less than 83% of the initial concentration in the organic phase. An inert hydrocarbon solvent is added to adjust the concentration of hexane in the mixture between 0-75% by volume based on total volume of reaction mixture. The process can be operated between 0-75% hexane beacause of the viscosity of the sulfonic acid at elevated temperatures. Lesser molecular weight oil soluble sulfonic acid has a viscosity such that an inorganic solvent diluent is unnecessary at elevated temperatures. Equivalent steps are the addition of hexane-water mixture, and the addition of hexane before the addition of water. The water wash removes sulfonic acids of low molecular weight which renders them soluble in water. This preferentially water-soluble sulfonic acid is of lesser value as a chemical intermediate.

The hexane-organic layer and the aqueous layer is intimately contacted for about 15 minutes at about 140° F. to wash sulfuric acid from the organic layer. The mixture is settled and the aqueous layer is removed and discarded. The aqueous wash removes sulfuric acid, sludge, and water soluble sulfonic acid.

After the water wash small amounts of sulfonic acid remain in the hexane layer. The sulfuric acid is commonly in the form of small droplets of aqueous acid suspended in the organic layer. The separation of the two layers is ineffective to remove this entrained sulfuric acid. Calcium carbonate is added to the organic layer which is about 100° F. to 150° F. to neutralize and remove residual entrained sulfuric acid. Thus, an amount of calcium carbonate of about 1.2 to about 3.0 moles per mole of the residual sulfuric acid is added to the oragnic layer. The calcium carbonate reacts with sulfuric acid for about 1 hour to 2 hours and produces calcium sulfate. The sulfonic acid in the organic phase remains essentially unneutralized. Both calcium carbonate and calcium sulfate are highly insoluble in inert organic solvents and water and are easily removed by filtration or centrifugation. Equivalent steps are addition of a calcium carbonate-SX-5W lubricating oil slurry, and addition of calcium carbonate and the lubricating oil separately.

Preferably, the calcium carbonate-organic phase mixture is agitated at about 100° F. to about 130° F. for one minute to two hours. A more preferred temperature and time for this is about 120° F. for about 120 minutes. The reaction driving force is mass transfer and adsorption. All solid impurities are removed by filtration or centrifugation.

The inert organic solvent is stripped, if necessary, from the mixture by heating the organic phase above the boiling point of inert organic solvent and blowing dry nitrogen through the organic phase.

The extremely pure sulfonic acid is recovered.

EXAMPLES

The following examples are illustrative, without implied limitation of our invention. These examples are laboratory scale preparations.

EXAMPLE I

A fifty-fifty (50/50) mixture by volume of hexane and 0.6 mole of crude polypropyl benzene sulfonic acid was recovered from a continuous sulfonation unit. Water was added to the mixture and an aqueous and organic layer was formed. Spent sulfuric acid and water-soluble polypropyl benzene sulfonic acid were dissolved in the aqueous layer. The aqueous layer was separated from the organic layer by drawing off the water layer using a centrifugal pump. The remaining organic layer containing hexane-polypropyl benzene sulfonic acid was again diluted to the 50% hexane level by volume. Calcium carbonate in a SX-5W lubricating oil slurry was added in the amount of 1.2 moles of $CaCO_3$ per mole of residual sulfuric acid ($H_2SO_4$) in the organic layer. The temperature was controlled at 100° F. for 1 hour while stirring in a closed 3 liter resin kettle. The kettle was equipped with a reflux condenser, twin turbine baffled agitation system and electric heat. After 1 hour, the temperature was raised to 220° F., while blowing in nitrogen, and held at that temperature until substantially all hexane was removed (about 1% of the hexane remained). The solution was filtered through a 4" vacuum funnel with Johns Manville 535 pad and sparkler filter paper. Sulfuric acid ($H_2SO_4$) was essentially gone at this stage. The following observations were noted:

| Filtration Rate | 6 gal/Ft$^2$-Hour |
|---|---|
| Filtration Capacity | Dry cake for full batch |
| Product Rate | $R_{250}$ = 2.2 gallon/Ft$^2$-Hr. |

The product of the process was overbased with magnesium oxide to a TBN of 405.

TBN is Total Base Number. This number corresponds to the amount of potassium hydroxide in milligrams equivalent to the unneutralized base found in the overbased sulfonate per gram of product.

EXAMPLE II

Polypropenyl sulfonic acid is used in Example II in the method found in Example I. The molecular weight range used was 400-500. The lubricating oil slurry was heated at 100° C. for 2 hours. The following observations were noted:

| Filtration Rate | 9 gallon/Ft$^2$-Hr. |
|---|---|
| Filtration Capacity | Dry cake for full batch |
| Product Rate | $R_{250}$ = 2 |

An overbased sulfonate was made with this product and magnesium oxide with a total base number of 403. The overbased sulfonate was 9.1% magnesium.

EXAMPLE III

A fifty-fifty (50/50) hexane mixture by volume of polypropyl benzene alkylates was charged to a continuous sulfonation unit. 20% sulfur trioxide ($SO_3$) by weight in sulfuric acid ($H_2SO_4$) was charged to the unit. Spent sulfuric acid ($H_2SO_4$) was continuously removed in a two phase non-aqueous system leaving a polypropenyl benzene sulfonic acid product containing 7.4% by weight residual sulfuric acid ($H_2SO_4$). At this stage, water was added to dilute the residual sulfuric acid ($H_2SO_4$) to 85% by weight, including the sulfuric acid ($H_2SO_4$) generated from unused sulfur trioxide ($SO_3$).

The aqueous phase was separated from the resultant two phase aqueous-organic system, leaving the organic phase containing 0.98% by weight sulfuric acid ($H_2SO_4$). Hexane was added to the organic phase followed by addition of Calcium Carbonate ($CaCO_3$). The resulting mixture was treated with SX-5W oil to reduce the viscosity of the sulfonic acid and also make a 30% by weight active product sulfonate. The product mixture was heated at 215° F. to strip the hexane. The hexane-stripped product was filtered to yield a sulfonic acid and oil product mixture containing less than 0.4%* by weight sulfuric acid.

* essentially no sulfuric acid remains; 0.4% $H_2SO_4$ is the lower detection limit.

EXAMPLE IV

The procedure of Example III was repeated except that following the addition of calcium carbonate ($CaCO_3$) the hexane solution was centrifuged and the calcium sulfate and excess calcium carbonate were separated. The hexane solution was heated at 215° F. to strip the hexane and SX-5W oil was added to yield the oil product mixture containing less than 0.4%* by weight sulfuric acid.

EXAMPLE V

A mixture of 50% hexane and polypropyl Benzene molecular weight from 500–600 was sulfonated using 20% by weight $SO_3$ in $H_2SO_4$, fuming $H_2SO_4$. A ratio of 2 moles $SO_3$ per mole of active alkylate charge was used. The material was continuously settled for a composition as follows:

| | |
|---|---|
| % hexane | 34.4 |
| % sulfonic acid (calc. as sodium soap) | 43.6 |
| % $H_2SO_4$ | 3.8 |
| % inert hydrocarbon lubricating oil | 18.2 |
| Equivalent weight (% in weight %) | 580 |

Water dilution took place and the product was settled in a plant tank. Soluble tars were drained from the lower aqueous phase. The analysis of this product was as follows:

| | |
|---|---|
| % hexane | 45.1 |
| % sulfonic acid (calc. as sodium soap) | 44.5 |
| % $H_2SO_4$ | 0.98 |
| % inert hydrocarbon lubricating oil | 9.41 |
| Equivalent weight (% in weight %) | 580 |

Hexane was added, in small amounts, 10% by weight, to remove tar like insolubles from the sulfonic acid crude. $CaCO_3$ was added to a reactor of the crude product, 2000 gallons, at a 3 to 1 mol ratio of $CaCO_3$ to residual $H_2SO_4$ while stirring at 120° F. for 15 minutes. SX-5W oil was added to the reactor while continuing the reaction and stirring. This took an additional 30 minutes. The reactor was heated to 220° F. to remove hexane and nitrogen was used as a stripping gas at the rate of 2000 SCFH per 2000 gallons. The crude product, hexane free, was filtered thru a conventional Sparkler filter and the resultant product analyzed and drummed. The analysis was:

| | |
|---|---|
| % hexane | 7.9 |
| % sulfonic acid (calc. as sodium soap) | 37.0 |
| % $H_2SO_4$ | less than 0.4* |
| % oil | 54.9 |
| Equivalent weight (% in weight %) | 580 |

Pure sulfonic acid is prepared in this procedure. The percent sulfonic acid is presented as sodium soap because of the analytical procedure used to analyze the material after purification. The product mixture prepared in accordance with Examples III, IV, and V was overbased with magnesium oxide (MgO) to yield a 440 TBN magnesium sulfonate.

It is significant to note from these examples that high total base numbers (TBN) in the range of 400 to 460 can be uniformly attained when overbasing the highly purified sulfonic acids produced by this process. This result has advantages over the typical production of sulfonic acids which can be overbased to attain total base numbers only in the 360 to 400 range. The sulfonates with higher TBN have better detergent and rust inhibiting properties than sulfonates with lower total base numbers such as 360 to 400.

The following Tables I and II illustrate the comparative advantages in the use of calcium carbonate rather than CaO in the process of this invention, when applied at a pilot plant.

Table I represents the filterability results achieved where calcium oxide was substituted for calcium carbonate in the process of this invention; Table II represents the purification results achieved when calcium carbonate is used in this invention:

TABLE I

Filterability of Purified Sulfonic Acids

| | | | Filtration | |
|---|---|---|---|---|
| Sulfonic Acid Used | Calcium Cpd. | Pressure (psig) | Rate Gal/Ft$^2$-Hr. | Capacity Gal-Ft$^2$ |
| 1. polypropyl benzene sulfonic acid (H) | $CaCO_3$ | 4 | 8.0 | 19.0 |
| 2. polypropyl benzene sulfonic acid (L) | $CaCO_3$ | 4 | 8.4 | 20.8 |
| 3. polypropyl benzene sulfonic acid (H) | CaO | | Could Not Filter*** | |
| 4. polypropyl benzene sulfonic acid (L) | CaO | | Could Not Filter*** | |

Table II shows the purification of the sulfonic acid obtained where calcium oxide is used in place of calcium carbonate:

TABLE II

Purification - Percentage of $H_2SO_4$ Remaining in the Sulfonic Acid Product

| Sulfonic Acid Used** | % $H_2SO_4$ Remaining | Calcium Cpd. |
|---|---|---|
| 1. polypropyl benzene sulfonic acid (H) | less than 0.4* | $CaCO_3$ |
| 2. polypropyl benzene sulfonic acid (L) | less than 0.4* | $CaCO_3$ |
| 3. polypropyl benzene | 0.4 | CaO |

TABLE II-continued

Purification - Percentage of H₂SO₄ Remaining in the Sulfonic Acid Product

| | Sulfonic Acid Used** | % H₂SO₄ Remaining | Calcium Cpd. |
|---|---|---|---|
| | sulfonic acid (H) | | |
| 4. | polypropyl benzene sulfonic acid (L) | 0.4 | CaO (% in weight %) |

*essentially no sulfuric acid remains; 0.4% H₂SO₄ is the lower detection limit.
**fifty (50) gallon batches were employed.
***the filter was completed clogged.

The letters "L" and "H" as appearing after the polypropyl benzene sulfonic acids indicate that the molecular weight of the particular acid was in the range of 500 to 600 and 800 to 900, respectively.

I claim:

1. A process for the purification of crude, oil soluble alkyl benzene sulfonic acid or polyalkenyl sulfonic acid which comprises:
   a. contacting the crude oil soluble alkyl benzene sulfonic acid or polyalkenyl sulfonic acid with an amount of water to form a separate aqueous phase containing less than about 85 percent by weight of sulfuric acid and preferentially water soluble sulfonic acid;
   b. separating said aqueous phase from the partially purified oil soluble alkyl benzene sulfonic acid or polyalkenyl sulfonic acid;
   c. contacting the partially purified oil soluble alkyl benzene sulfonic acid or polyalkenyl sulfonic acid with calcium carbonate to neutralize residual sulfuric acid and form a solid phase containing calcium sulfate, calcium carbonate and adsorbed impurities, and further characterized by being substantially free of calcium sulfonate, but not neutralizing significant amounts of sulfonic acid;
   d. separating the solid phase from the purified sulfonation reaction mixture; and
   e. recovering the purified oil soluble alkyl benzene or polyalkenyl sulfonic acid substantially free of sulfuric acid and calcium sulfate.

2. The process in claim 1 wherein the calcium carbonate mixture is contacted for about 120 minutes at about 120° F.

3. The process in claim 1 wherein an inert organic solvent is present in the crude sulfonation mixture was a diluent and carrier in the concentration between 0 and 75 percent by volume based on the total amount of reaction mixture, and wherein the inert organic solvent is removed from the reaction mixture before the sulfonic acid is recovered.

4. The process in claim 1 wherein the calcium carbonate is added in the form of a calcium carbonate-lubricating oil slurry and the sulfonic acid is recovered in a lubricating oil solution.

5. The process in claim 1 wherein the calcium carbonate is added to the crude oil soluble hydrocarbon sulfonic acid mixture separately from the lubricating oil.

6. The process in claim 1 wherein the calcium carbonate is in the form of finely divided particles whose size range from about 0.2 to about 5.0 microns.

7. The process in claim 1 wherein the sulfonation agent is separated from the crude oil soluble hydrocarbon sulfonic acid mixture prior to contacting the crude oil soluble hydrocarbon sulfonic acid mixture with water.

8. The process of claim 1 wherein the mole ratio of calcium carbonate to residual sulfuric acid is about 1.2–3.0:1.

* * * * *

UNITED STATES PATENT OFFICE
CERTIFICATE OF CORRECTION

Patent No. 4,321,214            Dated  March 23, 1982

Inventor(s)  Charles F. Nicolet

It is certified that error appears in the above-identified patent and that said Letters Patent are hereby corrected as shown below:

Column 3, line 11, "83%" should read --85%--.

Column 5, line 5, "Calcium Carbonate" should read --calcium carbonate--.

Column 5, line 26, "polypropyl Benzene" should read --polypropyl benzene--.

Column 5, line 64, "hexane and" should read --hexane, and--.

Column 8, line 12, "was a" should read --as a--.

Signed and Sealed this

Seventh Day of September 1982

[SEAL]

Attest:

Attesting Officer

GERALD J. MOSSINGHOFF

Commissioner of Patents and Trademarks